United States Patent
King

(10) Patent No.: US 6,271,421 B1
(45) Date of Patent: Aug. 7, 2001

(54) PROCESS FOR SELECTIVE MONO-DEBROMINATION OF POLYBROMOALKYL ARYL OR HETEROARYL KETONES

(75) Inventor: Anthony O. King, Neshanic Station, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/439,821

(22) Filed: Nov. 12, 1999

Related U.S. Application Data

(60) Provisional application No. 60/108,079, filed on Nov. 12, 1998.

(51) Int. Cl.$^7$ .................................................. C07C 45/65
(52) U.S. Cl. ...................... 568/316; 568/309; 568/312; 568/323; 549/505; 570/190
(58) Field of Search ..................................... 568/309, 312, 568/316, 323; 549/505; 570/190

(56) References Cited

U.S. PATENT DOCUMENTS 4,468,351   8/1984   Pirie et al. ..................... 260/245.2 R

FOREIGN PATENT DOCUMENTS

WO 98/11040   3/1998   (WO) .

OTHER PUBLICATIONS

Diwu, Tet. Letters 1998, 39 (28), 4987–90.
Scott et al., JACS, 1973, 95, 2708–09.
Merour et al., Tet. Letters 1991, 32 (22), 2469–70.
Kihara et al., Chem. Pharm. Bull. 1994, 42:67–73.
Ogawa et al., Chem. Pharm. Bull. 1992, 40:1315–1317.
Rival et al., Chem. Pharm. Bull. 1992, 40:1170–1176.
Konosu et al., Chem Pharm. Bull. 1990, 38:2476–2486.
Laufer et al., J. Med. Chem. 1994, 37:1894–1897.
Rosen et al., J. Med. Chem. 1990 33:3020–3023.
Bull et al., Tet Letters 1973, (44):4349–4352.
Posner et al., J. Amer. Chem. Soc. 1973, 95:3076–3077.
Lehman, Tet. Letters 1976, 987–988 (Translation plus original).
Bakos et al., Steroids 1993, 58 115–118.

*Primary Examiner*—Sreeni Padmanabhan
(74) *Attorney, Agent, or Firm*—Kenneth R. Walton; Melvin Winokur

(57) ABSTRACT

A process for selectively debrominating polybromoalkyl aryl ketones and polybromoalkyl heteroaryl ketones is disclosed. The process comprises contacting an alpha-polybrominated ketone with an alkali metal sulfite in the presence of a $C_2$–$C_6$ alkylcarboxylic acid to obtain a selectively mono-debrominated product.

20 Claims, No Drawings

PROCESS FOR SELECTIVE MONO-DEBROMINATION OF POLYBROMOALKYL ARYL OR HETEROARYL KETONES

This application claims the benefit of U.S. Provisional Application No. 60/108,079, filed Nov. 12, 1998.

FIELD OF THE INVENTION

The invention is directed to a process for the selective monodebromination of polybrominated alkyl aryl and alkyl heteroaryl ketones.

References are made in this application to various publications, the disclosures of which are hereby incorporated by reference in their entireties, in order to more fully describe the state of the art to which this invention pertains.

BACKGROUND OF THE INVENTION

Selectively brominated alkyl aryl and alkyl heteroaryl ketones are useful as intermediates in the preparation of various pharmaceuticals. Uses include, but are not limited to, intermediates in the preparation of norepinephrine potentiators (see, e.g., Kihara et al., *Chem. Pharm. Bull.* (1994), 42: 67—use of alpha-bromoacetophenone to prepare 4-phenyl-1,2,3,4-tetrahydroisoquinolin-4-ols), anti-tumor antibiotics (e.g., Ogawa et al., *Chem. Pharm. Bull.* (1992), 40: 1315—use of alpha-bromopropiophenone to prepare guanine 7-oxides), antimicrobials (e.g., Rival et al., *Chem. Pharm. Bull.* (1992), 40: 1170—use of alpha-bromo ketones; e.g., alpha-bromo-4-chloroacetophenone, to prepare imidazopyrimidine derivatives), antifungals (e.g., Konosu et al., *Chem. Pharm. Bull.* (1990), 38: 2476—use of alpha-bromo-2,4,-dihalopropiophenones to prepare triazole antifungals), cyclooxygenase and 5-lipogenase dual inhibitors (e.g., Laufer et al., *J. Med. Chem.* (1994), 37: 1894—use of phenacyl bromides to prepare pyrrolizine derivatives), and 5-$HT_3$ receptor antagonists (e.g., Rosen et al., *J. Med. Chem.* (1990), 33: 3020—use of alpha-bromo-2-methoxyacetophenone to prepare imidazolylthiazole derivative).

The base-catalyzed selective alpha-bromination of alkyl aryl ketones and alkyl heteroaryl ketones is generally difficult to achieve, because the presence of an alpha-bromine atom typically enhances the rate of further bromination at the alpha position. A substantially monobrominated product can be achieved by limiting the extent of reaction (e.g., by limiting the amount of brominating agent), but this results in a product mixture containing a substantial portion of unreacted starting ketone. On the other hand, if the bromination reaction is pushed to completion by the addition of more brominating agent, an overbrominated product results in which much of the product is di- and tri-brominated in the alpha-position.

One approach to obtaining only a monobrominated or only a dibrominated ketone product has been the selective monodebromination of overbrominated product. One method for selective monodebromination (see Bull et al., *Tetrahedron Letters* (1973), (44): 4349 and Posner et al., *J. Amer Chem. Soc.* (1973), 95: 3076) employs lithium dimethylcuprate, but this reagent is air, moisture and temperature sensitive, so that the reaction must be carried out under an inert atmosphere and at low temperature. Another method (see Lehman et al., *Tetrahedron Letters* (1976), 987 and Bakos et al., *Steroids* (1993), 58, 115) employs trimethylphosphite, but this reagent is environmentally unfriendly.

SUMMARY OF THE INVENTION

The present invention is directed to a process for the selective mono-debromination of polybromoalkyl aryl or heteroaryl ketones produced during bromination reactions, to the desired dibromo- or monobrominated product. The process comprises treating the polybrominated alkyl aryl or heteroaryl ketone with an alkali metal sulfite in alkylcarboxylic acid, under conditions effective to form the desired debrominated product. The process of the invention can be conducted in a straightforward manner using mild temperatures and does not require an inert atmosphere. The alkali metal sulfite reagent employed in the process is inexpensive, commercially available and environmentally safe.

DETAILED DESCRIPTION OF THE INVENTION

The present invention is a selective mono-debromination process which comprises contacting an alpha-polybrominated ketone selected from a compound of Formula I and a compound of Formula II:

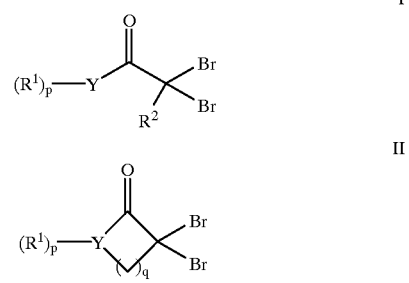

with an alkali metal sulfite in the presence of a $C_2$–$C_6$ alkylcarboxylic acid to obtain a selectively mono-debrominated product, wherein:

Y is aryl or heteroaryl having at least one ring heteroatom selected from O and S;

$R^1$ is halo, $C_1$–$C_6$ alkyl, $C_1$–$C_6$ haloalkyl, $C_1$–$C_6$ alkoxy, nitro, cyano, $SO_2R^a$, or $CO_2R^a$;

$R^2$ is hydrogen, bromo, or $C_1$–$C_6$ alkyl;

$R^a$ is $C_1$–$C_6$ alkyl; and p and q are each independently integers from 0 to 4.

In a first aspect of the process of the invention, the alpha-polybrominated ketone reactant is the compound of Formula I, and the mono-debrominated product comprises a compound of Formula III:

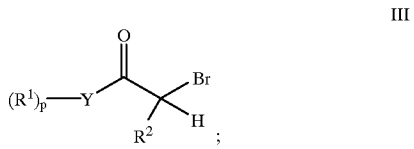

and all other variables and features are as originally set forth above.

In a second aspect of the process of the invention, the alpha-polybrominated ketone reactant is the compound of Formula II and the mono-debrominated product comprises the compound of Formula IV:

IV

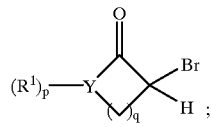

and all other variables and features are as originally set forth above.

In a third aspect of the process of the invention, Y is phenyl or a 5–6 membered aromatic heterocycle or a benzo-fused version thereof, having 1 to 3 ring heteroatoms selected from O and S; and all other variables and features are as originally set forth above or as set forth in either the first or the second aspect.

In another aspect of the process of the invention, the alkylcarboxylic acid is a $C_2$–$C_3$ alkylcarboxylic acid; and all other variables and features are as originally set forth above or as set forth in any one of the first, second, and third aspects.

In still another aspect of the process of the invention, the alkylcarboxylic acid is acetic acid and the alkali metal sulfite is sodium sulfite; and all other variables and features are as originally set forth above or as set forth in any one of the first, second, and third aspects.

In still another aspect of the process of the invention, p is an integer from 0 to 2 (e.g., p is 0 or 1; or p is 0; or p is 1); and all other variables and features are as originally set forth above or are as set forth in any one of the preceding aspects.

In still another aspect of the process of the invention, q is an integer from 2 to 4 (e.g., q is 2 or 3; or q is 2; or q is 3) and all other variables and features are as originally set forth above or are as set forth in any one of the preceding aspects.

In one embodiment, the present invention is a process for preparing a dibromomethyl ketone of Formula V:

V

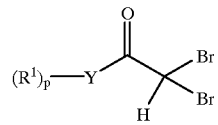

wherein:
  Y is aryl or heteroaryl having at least one ring heteroatom selected from O and S;
  $R^1$ is halogen, $C_1$–$C_6$ alkyl, $C_1$–$C_6$ haloalkyl, $C_1$–$C_6$ alkoxy, nitro, cyano, $SO_2R^a$, or $CO_2R^a$;
  $R^a$ is $C_1$–$C_6$ alkyl; and
  p is an integer from 0 to 4;
wherein the process comprises:
  (A) brominating a methyl aryl or heteroaryl ketone to obtain a reaction mixture comprising di- and tri-bromomethylketones of Formulas V and VI:

V

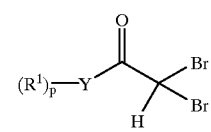

-continued

VI

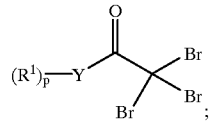

(B) contacting the reaction mixture obtained in (A) with an alkali metal sulfite in the presence of a $C_2$–$C_6$ alkylcarboxylic acid to selectively monodebrominate the tribromomethyl ketone.

In a first aspect of this embodiment of the process of the invention, Y is phenyl or a 5–6 membered aromatic heterocycle or a benzo-fused version thereof, having 1 to 3 ring heteroatoms selected from O and S; and all other variables and features are as originally set forth in this embodiment.

In another aspect of this embodiment, the alkylcarboxylic acid is a $C_2$–$C_3$ alkylcarboxylic acid; and all other variables and features are as originally set forth in the embodiment or as set forth in the first aspect of the embodiment.

In still another aspect of this embodiment, the alkylcarboxylic acid is acetic acid and the alkali metal sulfite is sodium sulfite; and all other variables and features are as originally set forth in the embodiment, or as set forth in the first aspect of the embodiment.

In still another aspect of this embodiment, p is an integer from 0 to 2 (e.g., p is 0 or 1; or p is 0; or p is 1); and all other variables and features are as originally set forth in the embodiment or are as set forth in any one of the preceding aspects.

In another embodiment, the process of the invention is a process for preparing an alpha-monobromoalkyl ketone selected from a ketone of Formula VI and a ketone of Formula VII:

VI

VII wherein:
  Y is aryl or heteroaryl having at least one ring heteroatom selected from O and S;
  $R^1$ is halogen, $C_1$–$C_6$ alkyl, $C_1$–$C_6$ haloalkyl, $C_1$–$C_6$ alkoxy, nitro, cyano, $SO_2R^a$, or $CO_2R^a$;
  $R^2$ is hydrogen or $C_1$–$C_6$ alkyl;
  $R^a$ is $C_1$–$C_6$ alkyl; and
  p and q are each independently integers from 0 to 4;
wherein the process comprises:
  (A) brominating an alkyl aryl or heteroaryl ketone selected from a ketone of Formula VIII and a ketone of Formula IX:

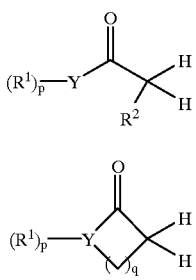

to obtain a reaction mixture comprising mono- and di-bromoalkyl ketones selected from (i) ketones of Formula I and Formula VI:

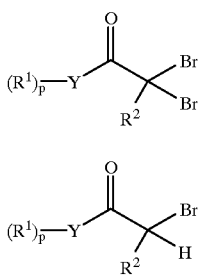

and (ii) ketones of Formulas II and VII:

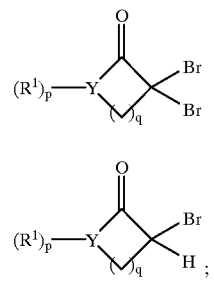

(B) contacting the reaction mixture with an alkali metal sulfite in the presence of a $C_2$–$C_6$ alkylcarboxylic acid to selectively monodebrominate the dibromoalkyl ketone to the alpha-monobromoalkyl ketone.

In a first aspect of this embodiment of the process of the invention, Y is phenyl or a 5–6 membered aromatic heterocycle or a benzo-fused version thereof, having 1 to 3 ring heteroatoms selected from O and S; and all other variables and features are as originally set forth in this embodiment.

In another aspect of this embodiment, the alkylcarboxylic acid is a $C_2$–$C_3$ alkylcarboxylic acid; and all other variables and features are as originally set forth in the embodiment or as set forth in the first aspect of the embodiment.

In still another aspect of this embodiment, the alkylcarboxylic acid is acetic acid and the alkali metal sulfite is sodium sulfite; and all other variables and features are as originally set forth in the embodiment, or as set forth in the first aspect of the embodiment.

In still another aspect of this embodiment, p is an integer from 0 to 2 (e.g., p is 0 or 1; or p is 0; or p is 1); and all other variables and features are as originally set forth in the embodiment or are as set forth in any one of the preceding aspects.

In still another aspect of this embodiment, q is an integer from 2 to 4 (e.g., q is 2 or 3; or q is 2; or q is 3) and all other variables and features are as originally set forth in the embodiment or are as set forth in any one of the preceding aspects.

The process of the invention (including all of its embodiments, aspects, and features herein described) optionally further comprises the step of recovering the selectively debrominated product resulting therefrom.

As used herein, the term "aryl" refers to an aromatic carbocyclic ring selected from phenyl and naphthyl.

The term "heteroaryl" refers to a stable 5- to 7-membered aromatic monocyclic ring system which consists of carbon atoms and from one to three heteroatoms selected from O and S, optionally fused with a benzo ring. The heteroaryl may be attached at any heteroatom or carbon atom which results in the creation of a stable structure. Suitable aromatic heterocycles include thiophene and furan. Suitable benzo-fused heterocycles include benzothiophene and benzofuran.

The term "$C_1$ to $C_6$ alkyl" means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl.

The term "$C_1$–$C_6$ alkoxy" means an —O-alkyl group wherein alkyl is $C_1$ to $C_6$ alkyl.

The term "halo" (which may alternatively be referred to as "halogen") refers to fluoro, chloro, bromo, and iodo (alternatively fluorine, chlorine, bromine and iodine).

The term "$C_1$–$C_6$ haloalkyl" (which may alternatively be referred to as "halogen substituted $C_1$–$C_6$ alkyl") means a $C_1$ to $C_6$ linear or branched alkyl group as defined above substituted with one or more halogens. Representative examples of suitable haloalkyls include the series $(CH_2)_{0-4}CF_3$ (i.e., trifluoromethyl, 2,2,2-trifluoroethyl, 3,3,3-trifluoro-n-propyl, etc.), tribromomethyl, 1-fluoroethyl, 2-fluoroethyl, 2,2-difluoroethyl 2-bromoethyl, 3,3,3-trifluoroisopropyl, 1,1,1,3,3,3-hexafluoroisopropyl, and per-fluorohexyl.

The term "$C_2$–$C_6$ alkylcarboxylic acid" refers to a compound of formula RCOOH wherein R is a linear or branched $C_2$–$C_6$ alkyl group. Suitable alkylcarboxylic acids include, acetic acid, propionic acid, butyric acid, valeric acid, isovaleric acid, and caproic acid.

As used herein, the term "contacting" means that the starting ketone(s), the sulfite, the alkylcarboxylic acid and other reagents or solvents being employed (if any) can be added to the reaction vessel concurrently, or sequentially in any order. In one embodiment, the starting ketone and the alkylcarboxylic acid are charged first (sequentially in either order or concurrently), followed by addition of the sulfite. In one aspect of this embodiment, the starting ketone is mixed with the alkylcarboxylic acid and the mixture is charged to the reaction vessel. In another aspect of this embodiment, the sulfite is added all at once after the starting ketone and alkylcarboxylic acid have been charged. In still another aspect, a portion of the sulfite is added at the start the reaction, and one or more additional portions are added during the course of the reaction, as needed to bring the reaction to completion.

The alkali metal of the alkali metal sulfite is suitably selected from sodium, potassium, and lithium. A class of alkali metals within this group comprises potassium and sodium. A sub-class is sodium.

The amount of alkali metal sulfite which may be employed in the process of the invention is typically in the range of from about 1.1 to about 5 mole equivalents per mole of starting ketone.

The amount of alkylcarboxylic acid employed in the process is typically in the range of from about 3 ml to about 20 ml per mole of starting ketone and may have water present in a range of from zero to about 5 ml per g of starting ketone.

The temperature at which the process is conducted is not critical, but a temperature in the range of from about 10 to about 30 C is suitable, and a temperature of from about 20 to 25 C is convenient.

The time of reaction will of course vary with, inter alia, the degree of reaction desired, the reaction temperature, and the choice and relative proportions of starting ketone, sulfite, and alkylcarboxylic acid. The reaction time is typically in the range of from about 1 to about 48 hours, and the reaction is typically conducted to completion. The progress of the reaction is typically monitored on a regular basis to avoid over-reduction which can occur with use of prolonged reaction times. After addition of the sulfite, the reaction mixture is sampled regularly and quenched when the desired composition is reached. When the sulfite is added in portions, the mixture is assayed before the next portion is added The starting polybrominated ketone reactant (i.e., dibrominated ketone(s), tribrominated ketone(s), or mixtures thereof) can be prepared by bromination of the corresponding ketone by conventional methods, such as those described or referred to in House, *Modern Synthetic Reactions*, 2d ed., (W. A. Benjamin, New York, 1972), pp. 459–478.

The following Examples further describe and illustrate the invention and its practice and are not to be construed as limiting the scope or spirit of the invention.

EXAMPLES 1–12

Methods 1–4 described below were the procedures employed for brominating alkyl aryl and alkyl heteroaryl ketones designated "A" resulting in the production of one or more brominated products designated "B" (monobromo-), "C" (dibromo-) or "D" (tribromo-), followed by selective mono-debromination of the polybromoalkyl aryl and polybromoalkyl heteroaryl ketone products. In general terms, A, B, C and D may be represented as follows:

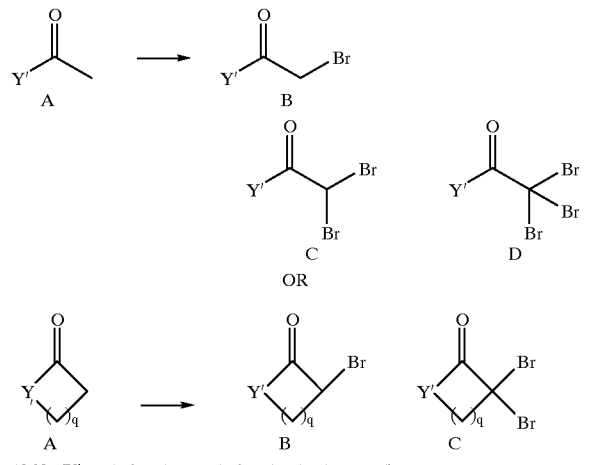

40,32 (Y' = substituted or unsubstituted aryl or heteroaryl)

The starting ketones A are identified in the Table below, which presents the results of the bromination/debromination procedures set forth in Methods 1–4. In the discussion of Methods 1–4 below, eq=equivalent; g=gram; h=hour; HPLC=high performance liquid chromatography; and ml=milliliter.

Method 1—A mixture of A, bromine (1.8 eq) and 10 ml of acetic acid per gram of A was stirred for 1 h. Water (5 ml/g of A) was added, and 3.8 eq of $Na_2SO_3$ was added all at once.

Method 2—The same conditions as described in Method 1 were used, except that 20 ml of acetic acid were used.

Method 3—A mixture of A, 5.5 eq of bromine, 20 ml of $CH_2Cl_2$/g of A was stirred for 20 h. The solvent was switched to 10 ml of acetic acid/g of A and 1.7–2.2 eq of $Na_2SO_3$ was added in 20% portions and the mixture was stirred for 21–26 h.

Method 4—A mixture of A, 1.3 eq of bromine and 10 ml of $CH_2Cl_2$/g of A was stirred for 43 h. The solvent was switched to 3 ml acetic acid/g of A and 2.1 eq of $Na_2SO_3$ were added all at once, followed by 0.11 ml of water/g of A.

The reactions in the above-described Methods were monitored by HPLC. A sample was taken from the reactor every one to two hours after the addition of the sulfite and diluted before injection onto the HPLC column. Once the reaction rate had slowed substantially, the reaction mixture was allowed to age overnight to completion. At this point the amount of active sulfite remaining should be very low based on the reaction rate. In cases where the sulfite was added in portions, the reaction was sampled 1 to 2 hours after each sulfite addition to ascertain the amount of over brominated material remaining before addition of the next portion of sulfite. The ratio of the products to the starting material was determined based on the HPLC area %. When the desired reduction level was achieved (typically when <1% of the HPLC area % was due to each of the two by-products), the reaction was quenched with water, and the organic products extracted into an organic solvent such as toluene, ethyl acetate, methyl t-butyl ether or methylene chloride. The organic solvent was washed with water and then with aqueous bicarbonate to remove all acetic acid. The organic solution containing the desired product was concentrated via distillation in vacuo.

While the foregoing specification teaches the principles of the present invention, with an example provided for the purpose of illustration, the practice of the invention encompasses all of the usual variations, adaptations and/or modifications that come within the scope of the following claims.

TABLE

| Example No. Ketone A | Method | A/B/C/D | $Na_2SO_3$[a] (eq) | A/B/C/D | Time (h) | Yield (%) |
|---|---|---|---|---|---|---|
| 1. Acetophenone | 1 | 0.1/25.8/74.1/0.0 | 3.8 | 0.3/99.7/0.0/0.0 | 5 | 86 |
| 2. 3-fluoroacetophenone | 1 | 0.1/27.2/72.7/0.0 | 3.8 | 0.4/99.5/0.1/0.0 | 2 | 84 |
| 3. 2-chloroacetophenone | 1 | 0.1/24.1/75.8/0.0 | 3.8 | 1.4/98.3/0.3/0.0 | 6 | 85 |

TABLE-continued

| Example No. Ketone A | Method | A/B/C/D | Na$_2$SO$_3$[a] (eq) | A/B/C/D | Time (h) | Yield (%) |
|---|---|---|---|---|---|---|
| 4. 4-nitroacetophenone | 1 | 0.1/30.1/69.8/0.0 | 3.7 | 0.2/99.5/0.3/0.0 | 5.5 | 78 |
| 5. 1-indanone | 2 | 0.0/17.0/83.0/0.0 | 3.9 | 0.6/99.2/0.2/0.0 | 4 | 92 |
| 6. 1-tetralone | 1 | 0.0/20.0/80.0/0.0 | 4.8 | 0.2/99.1/0.7/0.0 | 42 | 95 |
| 7. 1-benzosuberone | 2 | 0.0/25.8/74.2/0.0 | 3.8 | 0.0/99.5/0.5/0.0 | 20 | 93 |
| 8. 2-acetylfuran | 1 | 0.5/34.8/64.6/0.0 | 3.8 | 0.5/99.5/0.0/0.0 | 1.5 | 69 |
| 9. Acetophenone | 3 | 0.0/1.1/66.1/32.8 | 1.7 | 0.0/0.9/99.1/0.0 | 21 | 95 |
| 10. 2-chloroacetophenone | 3 | 0.0/0.0/74.0/26.0 | 2.2 | 0.0/1.0/99.0/0.0 | 26 | 92 |
| 11. 4-fluoroindanone | 4 | 0.6/68.5/30.9/0.0 | 2.1 | 0.9/98.4/0.7/0.0 | 3.5 | 96 |
| 12. 4,6-difluoroindanone | 4 | 0.5/64.1/35.4/0.0 | 2.3 | 0.6/98.0/1.4/0.0 | 7 | 95 |

[a]Based on mole percent of starting ketone

What is claimed is:

1. A selective mono-debromination process which comprises contacting an alpha-polybrominated ketone selected from a compound of Formula I and a compound of Formula II:

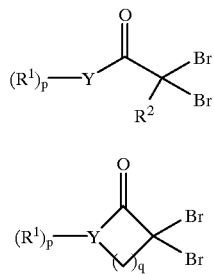

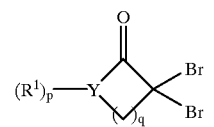

with an alkali metal sulfite in the presence of a C$_2$–C$_6$ alkylcarboxylic acid to obtain a selectively mono-debrominated product, wherein:

Y is aryl or heteroaryl having at least one ring heteroatom selected from O and S;

R$^1$ is halo, C$_1$–C$_6$ alkyl, C$_1$–C$_6$ haloalkyl, C$_1$–C$_6$ alkoxy, nitro, cyano, SO$_2$R$^a$, or CO$_2$R$^a$;

R$^2$ is hydrogen, bromo, or C$_1$–C$_6$ alkyl;

R$^a$ is C$_1$–C$_6$ alkyl; and p and q are each independently integers from 0 to 4.

2. The process of claim 1, wherein the alpha-polybrominated ketone reactant is the compound of Formula I, and the mono-debrominated product comprises a compound of Formula III:

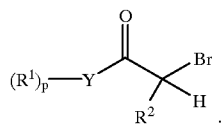

3. The process of claim 1, wherein the alpha-polybrominated ketone reactant is the compound of Formula II and the mono-debrominated product comprises the compound of Formula IV

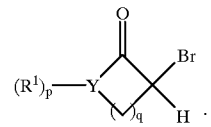

4. The process of claim 1, wherein the alkylcarboxylic acid is a C$_2$–C$_3$ alkylcarboxylic acid.

5. The process of claim 1, wherein the alkylcarboxylic acid is acetic acid and the alkali metal sulfite is sodium sulfite.

6. The process of claim 2, wherein the alkylcarboxylic acid is acetic acid and the alkali metal sulfite is sodium sulfite.

7. The process of claim 3, wherein the alkylcarboxylic acid is acetic acid and the alkali metal sulfite is sodium sulfite.

8. The process of claim 1, wherein Y is phenyl or a 5–6 membered aromatic heterocycle or a benzo-fused version thereof, having 1 to 3 ring heteroatoms selected from O and S.

9. The process of claim 8, wherein the alkylcarboxylic acid is a C$_2$–C$_3$ alkylcarboxylic acid.

10. The process of claim 9, wherein the alkylcarboxylic acid is acetic acid and the alkali metal sulfite is sodium sulfite.

11. A process for preparing a dibromomethyl ketone of Formula V:

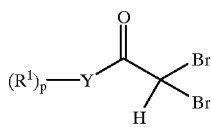

wherein:

Y is aryl or heteroaryl having at least one ring heteroatom selected from O and S;

R$^1$ is halo, C$_1$–C$_6$ alkyl, C$_1$–C$_6$ haloalkyl, C$_1$–C$_6$ alkoxy, nitro, cyano, SO$_2$R$^a$, or CO$_2$R$^a$;

R$^a$ is C$_1$–C$_6$ alkyl; and p is an integer from 0 to 4;

wherein the process comprises:

(A) brominating a methyl aryl or heteroaryl ketone to obtain a reaction mixture comprising di- and tri-bromomethylketones of Formulas V and VI:

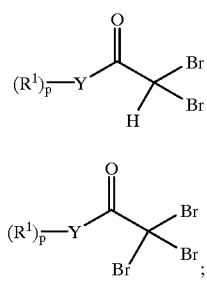

V

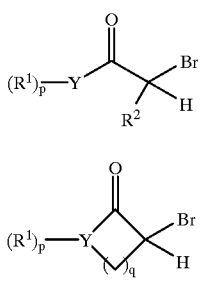

VI and (B) contacting the reaction mixture obtained in (A) with an alkali metal sulfite in the presence of a $C_2$–$C_6$ alkylcarboxylic acid to selectively monodebrominate the tribromomethyl ketone.

12. The process of claim 11, which further comprises recovering the dibromomethyl ketone.

13. The process of claim 11, wherein Y is phenyl or a 5–6 membered aromatic heterocycle or a benzo-fused version thereof, having 1 to 3 ring heteroatoms selected from O and S.

14. The process of claim 11, wherein the alkylcarboxylic acid is a $C_2$–$C_3$ alkylcarboxylic acid.

15. The process of claim 14, wherein the alkali metal sulfite is sodium sulfite and the alkylcarboxylic acid is acetic acid.

16. A process for preparing an alpha-monobromoalkyl ketone selected from a ketone of Formula VI and a ketone of Formula VII:

VI

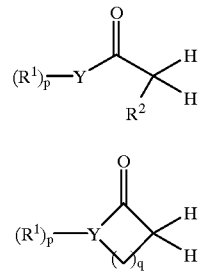

VII wherein:

Y is aryl or heteroaryl having at least one ring heteroatom selected from O and S;

$R^1$ is halo, $C_1$–$C_6$ alkyl, $C_1$–$C_6$ haloalkyl, $C_1$–$C_6$ alkoxy, nitro, cyano, $SO_2R^a$, or $CO_2R^a$;

$R^2$ is hydrogen or $C_1$–$C_6$ alkyl;

$R^a$ is $C_1$–$C_6$ alkyl; and p and q are each independently integers from 0 to 4;

wherein the process comprises:

(A) brominating an alkyl aryl or heteroaryl ketone selected from a ketone of Formula VIII and a ketone of Formula IX:

VIII

IX to obtain a reaction mixture comprising mono- and di-bromoalkyl ketones selected from (i) ketones of Formula I and Formula VI:

I

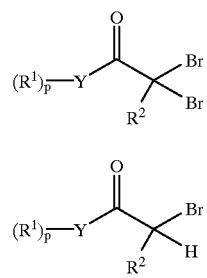

VI and (ii) ketones of Formulas II and VII:

II

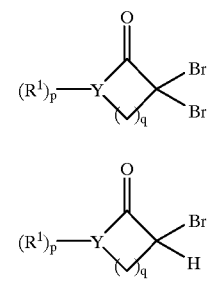

VII and (B) contacting the reaction mixture with an alkali metal sulfite in the presence of a $C_2$–$C_6$ alkylcarboxylic acid to selectively monodebrominate the dibromoalkyl ketone to the alpha-monobromoalkyl ketone.

17. The process of claim 16, which further comprises recovering the alpha-monobromoalkyl ketone.

18. The process of claim 16, wherein Y is phenyl or a 5–6 membered aromatic heterocycle or a benzo-fused version thereof, having 1 to 3 ring heteroatoms selected from O and S.

19. The process of claim 16, wherein the alkylcarboxylic acid is a $C_2$–$C_3$ alkylcarboxylic acid.

20. The process of claim 19, wherein the alkali metal sulfite is sodium sulfite and the alkylcarboxylic acid is acetic acid.

* * * * *